US00PP15219P3

(12) United States Plant Patent
Orton et al.

(10) Patent No.: US PP15,219 P2
(45) Date of Patent: Oct. 12, 2004

(54) DOGWOOD TREE NAMED 'RUTNUT'

(50) Latin Name: *Cornus florida L.*
Varietal Denomination: Rutnut

(75) Inventors: Elwin R. Orton, Millstone, NJ (US); David A. Gant, Wall Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 5 days.

(21) Appl. No.: 10/316,735

(22) Filed: Dec. 11, 2002

(65) Prior Publication Data

US 2004/0117881 P1 Jun. 17, 2004

(51) Int. Cl.[7] ..... A01H 5/00

(52) U.S. Cl. ..... Plt./220

(58) Field of Search ..... Plt./220

(56) References Cited

U.S. PATENT DOCUMENTS

PP8,214 P * 4/1993 Orton et al. ..... Plt./220

* cited by examiner

*Primary Examiner*—Anne Marie Grunberg
*Assistant Examiner*—June Hwu
(74) *Attorney, Agent, or Firm*—James A. Lucas; Driggs, Lucas, Brubaker & Hogg Co., LPA

(57) ABSTRACT

A cultivar of dogwood tree is characterized by a unique combination of red floral bracts and a dwarf rounded shape.

2 Drawing Sheets

Latin name of genus and species: *Cornus florida* L. var. *rubra* West.
Cultivar name: 'Rutnut'.

BACKGROUND OF THE INVENTION

This new cultivar is the product of a long standing detailed program of hybridization and selection of large-bracted dogwoods, in this instance from our native Eastern or *Cornus florida* seedlings which are carefully controlled, records carefully retained and characteristics analyzed for their differences and outstanding value as potential commercial varieties or cultivars.

As will be understood from the following, the program has resulted in many outstanding crosses which ultimately result in particularly attractive vegetative and floral parts, which appear on trees which are very floriferous and regular bearers.

We have selected the particular seedling hereof from certain progeny grown in a cultivated area and, as a result, have in turn caused the same to be asexually reproduced by stem cuttings in the vicinity of New Brunswick, N.J. The cultivar may also be so reproduced by budding and grafting. The claimed cultivar is stable and reproduced true to type in successive generation of asexual reproduction.

The reproduction and actual growth and selection of the new cultivar took place in the vicinity of New Brunswick, N.J. and has been found to be distinctive as to its winter-hardiness in that area, USDA Plant Hardiness Map Zone 6a.

As will be understood from the detailed description of the invention which appears hereinafter, the new cultivar is in fact outstanding and readily identified as being such, thus providing for a new variety which is identified botanically for the purposes hereof as *Cornus florida* L. Var. *rubra* West, and will be known commercially as 'Rutnut'.

With the foregoing in mind, the description which follows will be understood as clearly defining the new cultivar, the desirable characteristics of which are the result of such a program as has been heretofore suggested.

SUMMARY OF THE INVENTION

A cultivar of dogwood tree that is characterized by a unique combination of red floral bracts and a dwarf rounded shape. This new variety is distinguished from its parents, both of which grew to heights of 5 to 7 meters and exhibited flower heads with white bracts, whereas plants of "Rutnut" at maturity are very dwarf in size (less than 1 meter). It is believed to be the only dwarf *Cornus florida* to produce flower heads exhibiting pink-red floral bracts.

BRIEF DESCRIPTION OF THE DRAWINGS

This new cultivar of dogwood is illustrated by the accompanying photographic drawings, depicting the plant by the best possible color representation using color photography. All color references below are measured against The Royal Horticultural Society (R.H.S.) Colour Chart. Colors are approximate as color depends on horticultural practices, such as light level and fertilization rate, among others.

BOTANICAL DESCRIPTION OF THE INVENTION

Figure 1:
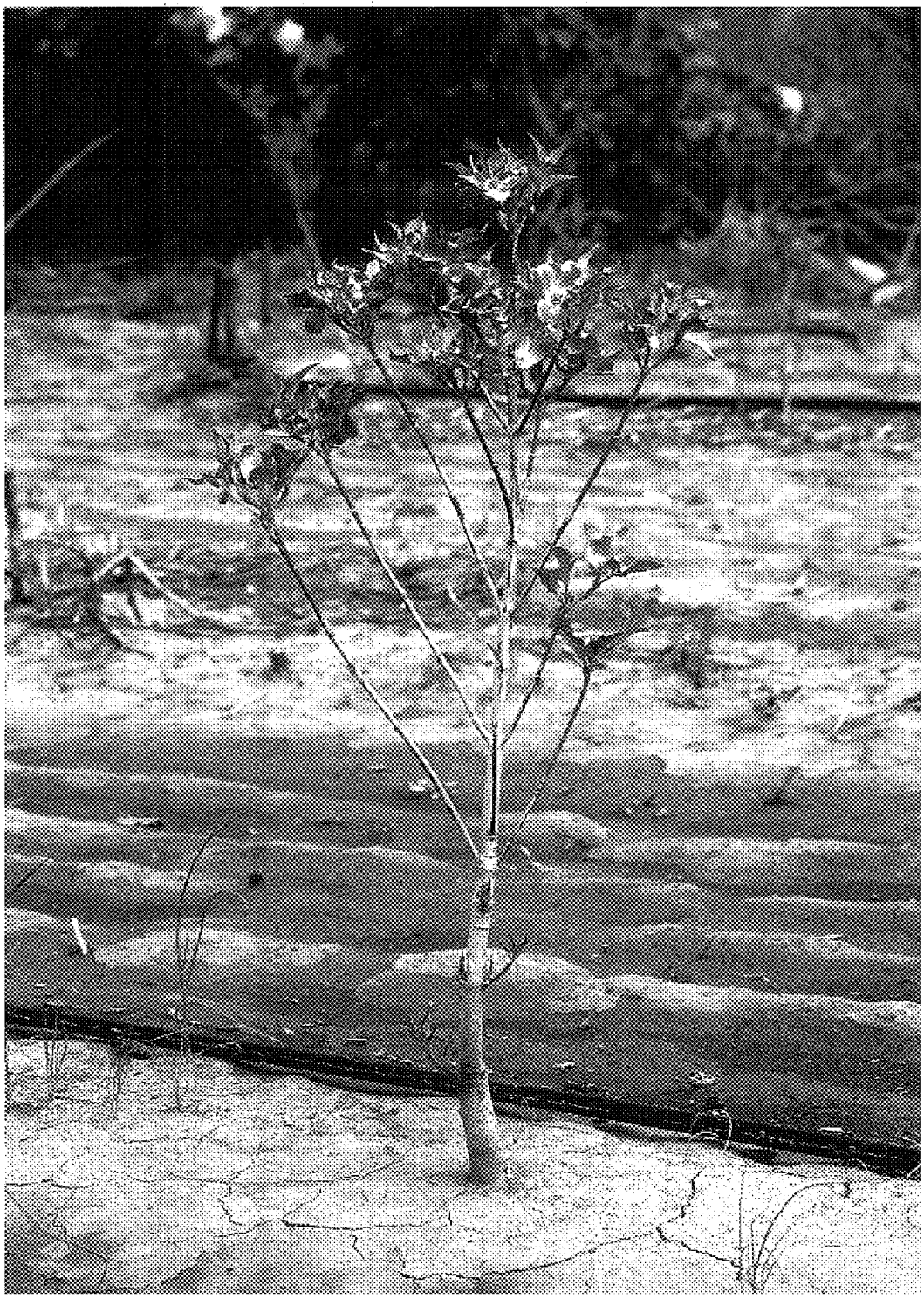
FIG. 1 is a two-year liner showing the dwarf nature of the tree and its precocious floral display of dark red floral bracts.
Figure 2:
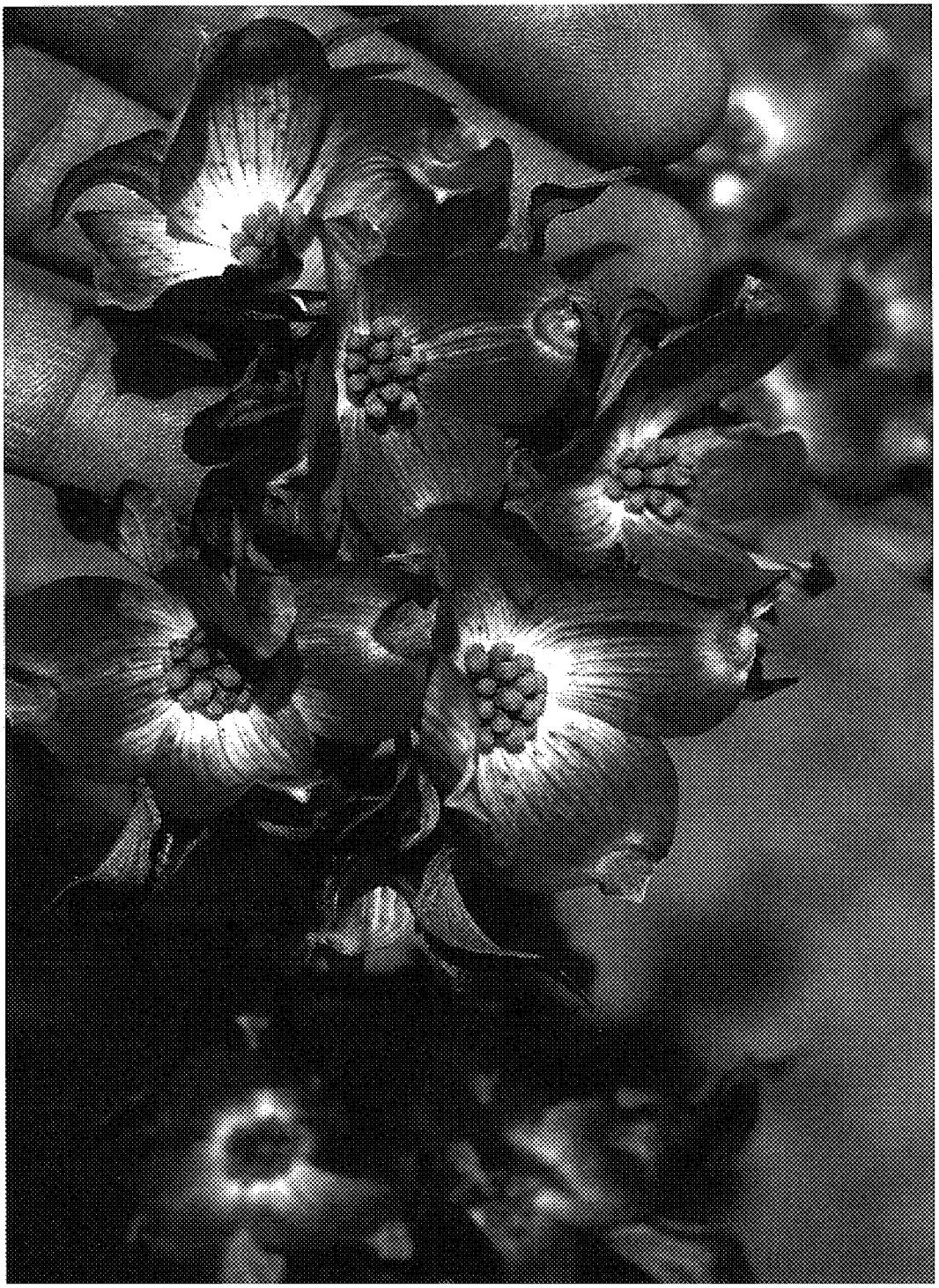
FIG. 2 discloses several flower heads at the time of floral display and indicates the color and shape of the floral bracts.

Origin: A seedling selection from the progeny of a controlled cross of two select seedlings, each of which originated from a cross of a plant of *C. florida* var. *rubra*×a plant of

*C. florida* 'Pygmy' (a white-bracted, non-patented cultivar), the *rubra* plants in the two initial crosses being unrelated in origin. Unpatented. Not subject of pending U.S. plant patent applications. Staminate parent of each parental hybrid was the cultivar 'Pygmy' (non-patented).

Reproduction took place in the vicinity of New Brunswick, N.J.

Classification: Botanic name: *Cornus florida* L. var. *rubra* West. Commercial name: 'Rutnut'.

Tree: Dwarf and rounded in shape. Is the first truly dwarf cultivar of var. *rubra* to be introduced to commerce, a five-year tree typically being 0.71 M tall and 0.61 M wide, or approximately one-half the typical size of a five-year plant of 'D-376-15', a patented (U.S. Plant Pat. No. 8,214) red-bracted clone of *C. florida* which develops a rounded, compact habit of growth considered semi-dwarf relative to standard clones (unpatented) of *Cornus florida* var. *rubra,* such as 'Sweetwater', 'Spring Song', 'Prosser Red', and the patented *rubra* clone 'Cherokee Chief', U.S. Plant Pat. No. 1,710 as well as white-bracted cultivars, such as 'Cherokee Princess' and 'Springtime'. Vegetative and floral parts have been fully winter-hardy at New Brunswick, N.J., USDA Plant Hardiness Zone 6a. Very floriferous. Regular bearer. A five-year plant of 'Rutnut' is about 76–91.5 cm tall with a spread of 61 cm in comparison to the white-bracted, non-patented cultivar 'Pygmy' which at five years averages 61–76 cm tall with a spread of 45.7 cm.

Trunk: Smooth as a young plant but bark becomes shaggy with age as is typical for plants of *C. florida.* Color of trunk or bark is 199D (Greyed Green Group on the R.H.S. Colour Chart of The Royal Horticultural Society, London).

Branches: Smooth, small to medium, with a high number of side branches which causes the tree to be dwarf and rounded; older branches ranging in color from 165A (Greyed Orange Group) to 200A (Brown Group); new tip growth being 146A (Yellow-Green Group).

Leaves:

*Ovate, with broadly attenuate base and apiculate tip.*—Length 6.3 to 12.2 cm (ave.=10.4 cm). Width at widest point 4.1 to 7.3 cm (ave.=6.01 cm). Petiole length 8 to 18 mm (ave.=12); Width 12 mm. Number of primary veins per leaf 10–12 (ave.=10.9). Margins entire.

*Color.*—Upper surface is closest to 137A (Green Group) but slightly darker. Lower surface is between 138B and 138C (Green Group); lower surface contains minute white pubescence, slightly longer along veins than on remainder of surface.

*Fall color.*—Typical of most *C. florida,* a showy display of green, yellow, orange and a red which is typical of most *rubra* varieties.

Flower buds: Medium size, nearly globose — height and width range from 4.0–5 mm. True flowers are tiny and relatively inconspicuous (each with four minute petals that are greenish-white in color). They are borne in dense heads, and are enclosed over winter by four involucral bracts that subtend the true flowers. Plants of 'Rutnut' are self-incompatible, as are all plants of *C. florida.*

Involucral, or floral bracts:

*Color.*—When fully expanded: Upper surface 59C to 59D (Red-Purple Group); lower surface 59D (Red-Purple Group). Basal 10% of bract surface is White Group 155D.

*Size and shape.*—When the floral bracts are fully expanded, the diameter of the involucre from tip to tip of the opposing inner bracts is about 7.53 cm. The diameter of the involucre as measured from tip to tip of the opposing outer bracts is approximately 7.11 cm. The average length of the inner and outer bracts is about 3.59 cm and 3.38 cm, respectively. The width of the inner and outer bracts at their widest point is about 2.71 cm and 3.59 cm, respectively. In general, the outer bracts are nearly equal in length and width and are broadly tapered at the base, whereas the inner bracts are longer than wide and are more narrowly tapered at the base. In general, the floral bracts would be considered obovate with an abruptly acute tip. The margin of the floral bracts is entire. The surface of the floral bracts has a soft ridged texture due to the prominent parallel veination. The basal one-third of adjacent bracts slightly overlap.

Peduncle: Each flower head is borne on a peduncle, the average length of which is about 2.15 cm at the time of flowering and/of floral display. The average peduncle length will vary slightly from year to year. Color is Green Group 137D.

Flowering and floral display: The period of floral display (floral bracts) is typical of that for most plants of *C. florida;* i.e., occurring in late April and early May in the vicinity of New Brunswick, N.J., and extending for a period of 12–17 days, depending on weather conditions. Anthesis of the tiny, relatively inconspicuous, true flowers commences two to four days after the onset of the ornamental display of the large floral bracts and continues for about seven days, depending on weather conditions. The average number of true flowers per flower head in our new intraspecific hybrid is about 14.7, whereas those of the patented clone 'D-376-15', which also bears red bracts (184C, Grey-Purple Group), is about 19.7. This characteristic is quite consistent from year to year. The mature size of 'Rutnut' is expected to be about one-half that of 'D-376-15'; i.e. about 1.7 m tall and 1.7 m wide. The flower has no detectable fragrance. Average flower head diameter of over-wintering flower buds is 3 mm. Average diameter of flower head at start of flowering period is 4–6 mm. Flower petals: four per flower. Length: about 2 to 3 mm. Width: about 1.25 mm. Apex: rounded. Margin: Entire. Color: Just prior to anthesis, both surfaces Yellow-Green Group 144C. Fully open, both surfaces Yellow-green Group 151D.

Reproductive organs: Features are inconspicuous. Ovary: inferior and bilocular with each locule having one ovule. Length: about 9 mm. Width: about 6 mm; Style is about 1.75 to 2.25 mm in length and 0.25 mm in diameter. The color of the style is closest to Yellow_Green Group 149A. Sepals: four per flower. Cannot be seen at the time of flowering unless the flower is dissected. Since the ovary is inferior, the sepals are readily observed at the tip of the mature fruit in September. To the naked eye, the sepals appear as equilateral triangles, each side of which is about 1 mm in length. Under 10× magnification, the sides and tip of the sepals can be seen to be slightly rounded and the basal 20 percent of adjacent sepals are fused. The color of the sepals on the mature fruit is Brown Group 200A. Petals: four per flower. Length: about 2 to 3 mm. Width: about 1.25 mm. apex: rounded. Margin: Entire. Color: Just prior to anthesis, both surface Yellow- Green Group 144C. Fully open, both surface Yellow-Green Group 151D. Stamens: Four per flower. Filament: Length: about 1.8 to 2 mm. Width: about 0.2 mm. Anther: Color: Yellow Group 11C. Pollen: closest to Yellow Group 11B.

Fruit: The fruit are elongate, approximately 9 to 13 mm long and bright red, RHS 45A and/or RHS 46B, (Red Group) as is rather typical of the fruit of most plants of *C. florida*. Fruit: Shape/type: Oblong drupe. Length: about 1.1 cm. Diameter: about 0.8 cm. Texture: Smooth. Color of pericarp of fruit: Red Group 46B. Seeds: Shape ovoid. Texture: horizontal furrows on opposing sides clearly delineate the two locules. Color: Freshly cleaned and dried seed closest to Greyed-Orange Group 146B.

Resistance to insects: The relative resistance, or susceptibility, of plants of 'Rutnut' to the various insect pests known to attack plants of *C. florida* is expected to be typical of that of plants of most cultivars of *C. florida*.

Diseases: The relative resistance, or susceptibility, of plants of 'Rutnut' to the various disease organisms known to attack plants of *C. florida* is assumed to be typical of that exhibited by most plants of *C. florida* but little information is available at this time.

We claim:

1. A new and distinct cultivar of dogwood tree, substantially as herein shown and described, characterized particularly as to novelty by the unique combination of its red floral bracts and the truly dwarf rounded habit of the tree.

* * * * *